564-63 SR
3/4/86 CF H 000,038

United States Statutory Invention Registration [19]

[11] Reg. Number: H38
[45] Published: Mar. 4, 1986

Radel et al.

[54] PROCESS FOR THE PREPARATION OF UREA AND ITS DERIVATIVES FROM CO, NO, AND A HYDROGEN SOURCE

[75] Inventors: Robert J. Radel; Yong K. Kim, both of Florence, Ala.

[73] Assignee: Tennesee Valley Authority, Muscle Shoals, Ala.

[21] Appl. No.: 754,555

[22] Filed: Jul. 15, 1985

[51] Int. Cl.[4] ..... C07C 126/00; C07C 127/01
[52] U.S. Cl. ..... 564/63; 564/65

*Primary Examiner*—John F. Terapane
*Assistant Examiner*—Howard J. Locker
*Attorney, Agent, or Firm*—Robert A. Petrusek

[57] ABSTRACT

A process for the preparation of urea and its derivatives by reacting CO, NO, and a hydrogen source over a supported noble metal catalyst at atmospheric pressure is described. Preferably, stoichiometric amounts of reactory gases are used. Reaction temperatures are in the range of 75° C. to 225° C.

9 Claims, 1 Drawing Figure

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

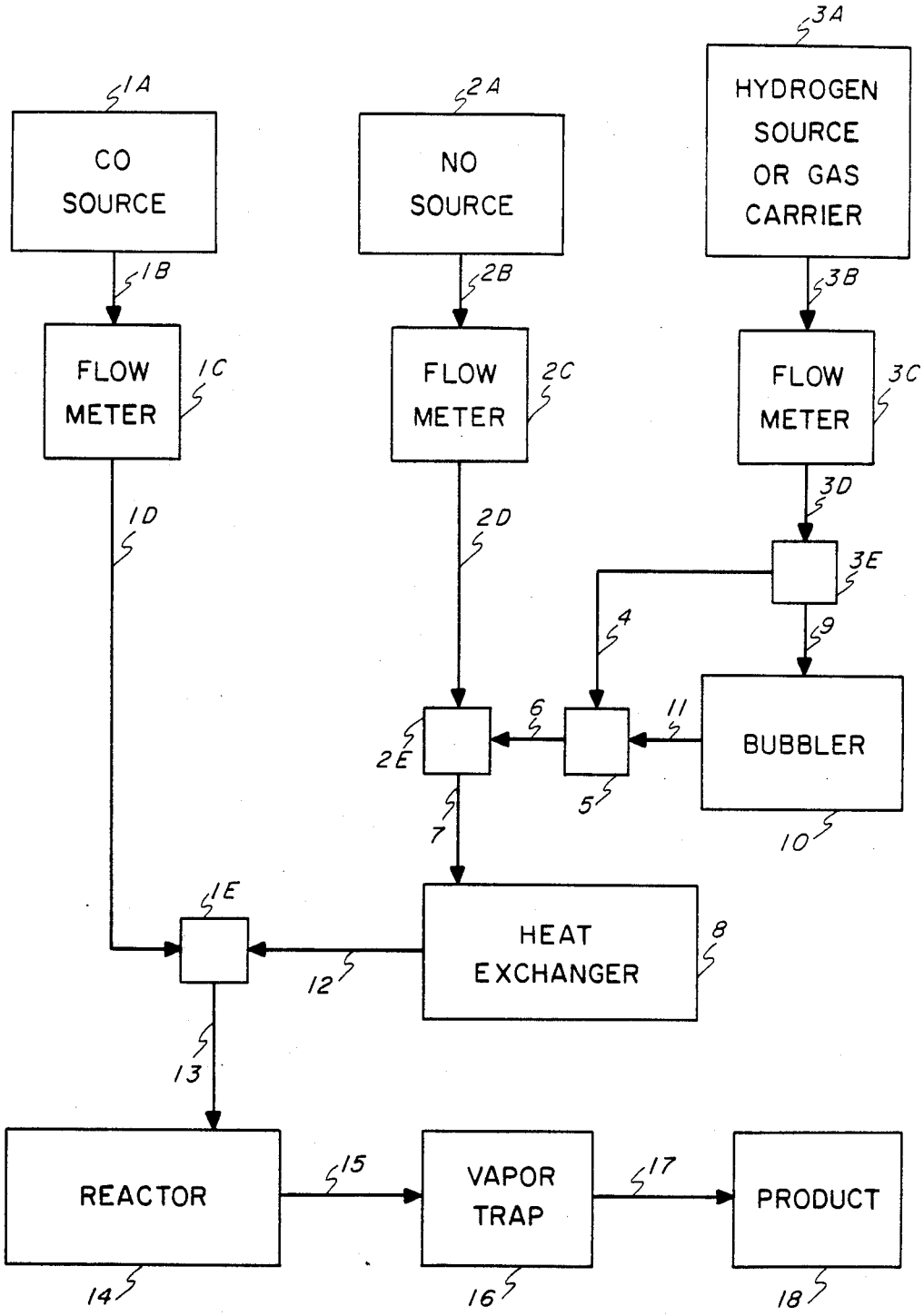
CO SOURCE
NO SOURCE
HYDROGEN SOURCE OR GAS CARRIER
FLOW METER
FLOW METER
FLOW METER
BUBBLER
HEAT EXCHANGER
REACTOR
VAPOR TRAP
PRODUCT
1A
1B
1C
1D
1E
2A
2B
2C
2D
2E
3A
3B
3C
3D
3E
4
5
6
7
8
9
10
11
12
13
14
15
16
17
18

PROCESS FOR THE PREPARATION OF UREA AND ITS DERIVATIVES FROM CO, NO, AND A HYDROGEN SOURCE

INTRODUCTION

The present invention describes a process for the preparation of urea and its derivatives at low temperatures and low pressures from CO, NO, and a hydrogen source as opposed to the prior art methods which utilize both high temperatures and high pressures, thereby resulting in a significant reduction in capital and energy costs for the process. More particularly, the process of the instant invention relates to the synthesis of urea and its derivatives by reacting carbon monoxide, nitric oxide, and a hydrogen source (such as methanol, water, or hydrogen) in the presence of a catalytic amount of a noble metal (such as palladium or rhodium) dispersed on an inert, inorganic support at temperatures between 75° C. and 225° C. and at atmospheric or near atmospheric pressure.

BACKGROUND OF THE INVENTION

1. Field of the Invention

Many prior-art processes have been developed for the preparation of urea and its derivatives using high temperature/high pressure processes and various feedstock chemicals, such as $CO_2$ $NH_3$, etc.

2. Description of the Prior Art

German Offen. No. 2,809,858 describes a process for reacting nitric oxide or nitrous oxide with carbon monoxide and hydrogen at 200° C. to 600° C. over Pd, Pb, Rh, or Monel catalysts to give ammonium cyanate. This process requires further conversion of the ammonium cyanate to urea and high energy requirements for the initial process. The process is generally carried out in dilute streams of helium, an expensive and valuable rare gas.

In a 1978 article, R. J. H. Voorhoeve and coworkers [*Science* 200, 759–761 (1978)]reacted carbon monoxide, nitric oxide, water, and hydrogen in a diluted stream of helium over ruthenium, rhodium, palladium, platinum, and iridium catalysts dispersed on alumina at 240° C. to 500° C. to give principally ammonium cyanate. Typically, the reactant gases (CO, NO, $H_2O$, $H_2$) comprised only 11.5% of the total gas flow, and of this only 17% was converted to ammonium cyanate. Further work by these same authors [*J. Catal.* 53 (2), 251–259 (1978)]indicates a maximum selectivity of 98% at 360° C. to 400° C. for ammonium cyanate from NO, CO, $H_2$ diluted in helium over Pt, Cu-Ni, Os, and ruthenium metal catalysts.

R. J. H. Voorhoeve, [*J. Catal.* 54 (1), 102–105 (1978)]also has reported the reduction of No over platinum catalysts at 650° C. to 800° C. to give principally nitrogen with some ammonia, hydrogen cyanide, and ammonium cyanate. Subsequent reports [*J. Catal.* 54 (2), 268–280 (1978)]indicate that the major products of the reaction of CO, NO, and $H_2$ over unsupported Pd, Ir, and Pt-10% Rh metal catalysts are ammonium cyanate and HNCO (isocyanic acid). The best yield of HNCO was 75% over iridium metal catalyst.

Cyanates (Belgium Pat. No. 876,483, Sept. 17, 1979) also have been produced by the catalytic hydrogenation of a mixture of nitric oxide and carbon monoxide in the presence of ammonia and a nobel metal, such as palladium, iridium, or mixtures of these. The formation of ammonium cyanate and isocyanic acid (HNCO) by a low-pressure catalytic process is described by Trimble et al in U.S. Pat. No. 4,174,377. In the reaction, a mixture of 0.3% NO, 5% CO, and 0.5% $H_2$ (with the balance being helium) is passed over a Pd catalyst at 550° C. and 40 L/h $m^2$. Conversion to cyanate compounds was 72.5%. All of the above processes emphasize the formation of cyanate rather than urea. Also, all are carried out at high temperatures and generally as dilute gas streams in helium, an expensive and rare gas. The production of urea would require further reaction of the ammonium cyanate.

Many important commercial applications have been developed for the urea produced from the present invention, for example, as in fertilizer preparation (both solid and liquid) and as resin monomers.

The process of the present invention provides a method for carrying out the reaction of nitric oxide, carbon monoxide, and a hydrogen source (such as methanol, hydrogen, or water) over palladium or rhodium noble metal catalysts or an inert support (such as alumina or silica) at low temperatures and pressures to directly produce urea and/or its derivatives.

SUMMARY OF THE INVENTION

The present invention provides a much improved catalytic process for the production of urea and its derivatives by reacting stoichiometric quantities of NO and a hydrogen source with carbon monoxide, which process is carried out at temperatures of 75° C. to 225° C. and pressure of about 1 atmosphere over a catalyst composed of a noble metal supported on an inert support. The molar ratio of hydrogen (or hydrogen source) to nitric oxide is controlled to produce the maximum yield of urea. .

OBJECTS OF THE INVENTION

It is therefore a primary object of the present invention to provide a process for the preparation of urea at low temperatures and pressures.

It is another object of the present invention to provide a novel reaction system useful in the formation of urea and its derivatives from carbon monoxide, nitric oxide, and a variable hydrogen source.

It is a further object of the present invention to provide a specific mechanism for the use of water or methanol as the above-mentioned hydrogen source.

Other objects and more specific advantages of the present invention, as compared with known prior art processes for the production of urea and derivatives, are: (1) reduction in the energy requirements for the process due to the exothermic nature of the reaction; (2) reduction in the capital costs of the process due to the low pressure of the reaction; (3) ease of recovery of the urea as either a solid or water solution; (4) the use of water (via the water-gas shift reaction) or other available hydrocarbons ($CH_4$, $CH_3OH$) as a hydrogen source; and (5) the direct formation of urea without the need for additional process steps.

These as well as other objectives and advantages of the present invention will become apparent from the description of the invention which follows and from the claims, it being understood, however, that this more detailed description is given by way of illustration and explanation only and not necessarily by way of limitation since various changes therein may be made by those skilled in the art without departing from the true spirit and scope of the present invention.

DESCRIPTION OF THE DRAWING

The present invention will be better understood by consideration of the following description taken in connection with the accompanying drawing in which a single FIGURE is a flowsheet of the laboratory-scale plant generally illustrating the principles of our process which result in the production of urea and its derivatives without the requirements for the employment therein of either high temperatures and high pressures.

Referring more specifically to the FIGURE, there are generally illustrated 3 parallel paths for the 3 principle feedstocks to the process from sources thereof through flowmeters to mixing means. For example, carbon monoxide flows from source 1A via line 1B through means for control of flow 1C and subsequently through line 1D to mixing means 1E at a flow rate of about 200 mL/min. Similarly, nitric oxide (32 mL/min) flow from source 2A to mixing means 2E as well as hydrogen (65 mL/min) source from 3A to mixing means 3E respectively. As illustrated, a carrier gas from 3A may be introduced via 3B and 3C into mixing means 3E directlty via line 3D and then via line 9 into aspirator or bubbler 10 and subsequently removed from bubbler 10 via line 11, means for control of flow 5, and line 6, into mixing means 2E. The principle purpose of bubbler 10 and later mentioned heat exchanger 8 is to provide means for controlling the saturation point of an alternate hydrogen source when the materials therefrom are subsequently combined in later-described reactor 14. Alternatively, a hydrogen source from 3A flowing through lines 3B and 3D and metered via 3C may be introduced into mixing means 3E and diverted around bubbler 10 via line 4 wherefrom it enters means for control of flow 5 and line 6 to mixing means 2E. In either embodiment, hydrogen source from 3A, introduced to mixing means 2E via line 6 is combined with nitric oxide source from 2A through lines 2B and 2D and means for control of flow 2C in mixing means 2E wherefrom it is introduced via line 7 to heat exchanger 8. The resulting mixed and heated nitric oxide and hydrogen exit heat exchanger 8 via line 12, and are combined, in mixing means 1E, with carbon monoxide from source 1A via lines 1B and 1D through means of control of flow 1C and subsequently introduced via line 13 into reactor 14. Reactor 14 may be in the form of a relatively low-pressure vessel since the highest pressures utilized in the practice of the instant invention normally do not exceed about 1 atmosphere. Reactor 14 is equipped with a palladium or rhodium noble metal catalyst on an inert support, as for example, alumina or silica.

In the case of our laboratory-scale apparatus, for the sake of convenience of construction said support was constructed of alumina. The reaction products from reactor 14 including urea and ammonium carbonate are withdrawn therefrom via line 15 and introduced into vapor trap 16 wherefrom ammonium carbonate is removed. The desired urea product is removed through vapor trap 16 via line 17 to product collection 18.

DESCRIPTION OF THE PREFERRED EMBODIMENTS

In accordance with the teachings of the instant invention, urea or a derivative thereof is produced by reacting in the vapor phase nitric oxide, carbon monoxide, and a hydrogen source at temperatures in the range of 75° C. to 225° C. and at pressures of about 1 atmosphere, in the presence of a catalyst comprising a noble metal such as palladium, rhodium, or mixtures thereof on an inert support. The synthesis of urea is carried out according to one of the following equations, depending on the hydrogen source employed:

$$CO + 2NO + 4H_2 \rightarrow H_2N\overset{\overset{\displaystyle O}{\|}}{C}NH_2 + 2H_2O \quad (1)$$

$$5CO + 2NO + 2H_2O \rightarrow NH_2\overset{\overset{\displaystyle O}{\|}}{C}NH_2 + 4CO_2 \quad (2)$$

$$2CO + 2NO + CH_3OH \rightarrow H_2N\overset{\overset{\displaystyle O}{\|}}{C}NH_2 + 2CO_2 \quad (3)$$

The reaction is exothermic and can be carried out at temperatures of 100° C. (a temperature at which the reaction is selfsustaining and no added heat is necessary) to about 225° C.

In general, the pressure is maintained at about 1 atmosphere. The composition of the gas influences the type of product obtained. If excess hydrogen is provided, more highly reduced products ($NH_3$, etc.) are formed. On the other hand, if the availability of hydrogen is restricted below the stoichiometric requirement, more highly polymerized products predominate (biuret, triuret, biuret cyanurate, etc.).

As indicated above, the reaction can be suitably performed by introducing the carbon monoxide, nitric oxide, and hydrogen source into contact with a catalyst at atmospheric or near atmospheric pressure and at moderate temperatures. Stoichiometric quantities of all gases and vapors may be employed. However, an excess of carbon monoxide may be employed, for example, in continuous processes where a suitable recycle of the carbon monoxide may be employed. The reaction will proceed at temperatures from about 75° C. to 225° C. It is generally preferred to operate the process at temperatures in the range of 100° C. to 150° C. to take advantage of the exothermic nature of the reaction. Heating and/or cooling means may be employed interior and/or exterior of the reaction to maintain the temperature within the desired range.

The hydrogen source used in the process may be hydrogen itself or in combination with other elements, such as alkanes, alcohols, or water.

Flow rates are generally dependent on the size of the reactor, the amount of catalyst and the stoichiometric requirements of the reaction. Flow rates may be adjusted slightly above and/or below the stoichiometric requirement so as to influence the composition of the product.

EXAMPLES

The following examples are provided to illustrate the invention in accordance with the principles of the present invention but are not to be construed as limiting the invention in any way except as indicated by the appended claims.

For the sake of convenience to the reader, the descriptions in the following examples will be read in terms of the elements shown in the single FIGURE and described in terms of the actual equipment so utilized; it being understood, of course, that these descriptions are not meant to limit the type and arrangment of process equipment which may be utilized in carrying out the instant invention in different scale or in different embodiments thereof.

EXAMPLE 1

A catalyst consisting of 0.25 g 5% $Rh/Al_2O_3$ and 0.25 g 5% Pd/(C) was charged to the glass reactor (14). The furnace was heated to 150° C. and the gas bubbler bath (8) and nitric oxide reaction coil (12) heated to 28° C. to provide the desired methanol vapor flow to the reactor. When these temperatures stabilized, the CO gas flow rate was adjusted to 200 mL/min and the NO flow rate adjusted to 32.4 mL/min via the flowmeters (4, 5, 6). The gas flows were continued for 2½ hours and the products collected in an ice bath trap. Upon completion of the reaction, additional solid was obtained from the reaction tube, just below the catalyst bed. The products were analyzed by HPLC using a $C_{18}$ Radial compression column and 5% methanol-water solvent. The results are indicated in Table 1 infra.

TABLE 1

| | Examples | | | | | | | |
|---|---|---|---|---|---|---|---|---|
| | 1 | 2 | 3 | 4 | 5 | 6 | 7 | 8 |
| Experimental Conditions | | | | | | | | |
| Catalyst, 0.5 g | ←0.25 g 5% $Rh/Al_2O_3$→ + 0.25 g 5% Pd/C | | | | | 5% $Rh/Al_2O_3$ | 5% Pd/C | 5% $Rh/Al_2O_3$ (recycled) |
| NO flow, ml/min | 32.4 | 32.4 | 32.4 | 32.4 | 32.4 | 32.4 | 32.4 | 32.4 |
| CO flow, ml/min | 200.0 | 200.0 | 200.0 | 200.0 | 200.0 | 200.0 | 200.0 | 200.0 |
| $CH_3OH$ flow, ml/min | 18.5 | 18.5 | 18.5 | 18.5 | 18.5 | 18.5 | 18.5 | 18.5 |
| Temp, °C. | 150.0 | 175.0 | 150.0 | 150.0 | 150.0 | 150.0 | 150.0 | 150.0 |
| Reaction time, hr | 2.5 | 2.5 | 1.75 | 2.0 | 6.0 | 6.0 | 6.0 | 6.0 |
| Recovered Products, g | | | | | | | | |
| Total | 1.9 | 1.23 | 1.27 | 0.45 | 3.82 | 3.66 | — | — |
| Urea | 0.69 | 0.61 | 0.45 | 0.19 | 2.04 | 1.68 | — | — |
| $(NH_4)_2CO_3H_2O$ | 0.62 | 0.54 | 0.72 | 0.23 | 1.77 | 1.88 | — | — |
| Biuret cyanurate | 0.79 | — | — | — | — | — | — | — |
| Triuret | — | — | — | — | — | — | — | — |
| % N, recovered | 15.0 | 13.0 | 18.0 | 6.0 | 19.0 | 17.0 | 0.0 | 0.0 |

EXAMPLES 2-6

The experiments were carried out as in example 1 supra, using temperatures in the range of 150° C. to 175° C., reaction times of between 1.75 and 6 hours, and palladium on carbon, rhodium on alumina or mixtures thereof as a catalyst.

EXAMPLE 7

This experiment was carried out as in example 1 1 supra, except that the catalyst consisted of 5% palladium on carbon alone. No solid products were obtained (see Table 1 supra).

EXAMPLE 8

This experiment was carried out as in Example 1 supra, using recycled rhodium on alumina as catalyst. No solid products were obtained.

EXAMPLES 9-16

These experiments were run as in Example 1 supra, except the solvent bubblers (7) were bypassed (9) and hydrogen gas was used in place of the methanol. Also, the hydrogen gas flow rate and temperature were varied to determine their effect on product formation. The conditions and results for the individual experiments are given in Table 2 infra.

TABLE 2

| | Examples | | | | | | | | | | | |
|---|---|---|---|---|---|---|---|---|---|---|---|---|
| | 9 | 10 | 11 | 12 | 13 | 14 | 15 | 16 | 17 | 18 | 19 | 20 |
| Experimental Conditions | | | | | | | | | | | | |
| Catalyst, 0.5 g | ←5% $Rh/Al_2O_3$→ | | | | | | | | 5% Pd/C | ←5% $Pd/Al_2O_3$→ | | |
| NO flow, ml/min | 32.4 | 32.4 | 32.4 | 32.4 | 32.4 | 32.4 | 32.4 | 32.4 | 32.4 | 32.4 | 32.4 | 32.4 |
| CO flow, ml/min | 200.0 | 200.0 | 200.0 | 200.0 | 200.0 | 200.0 | 200.0 | 200.0 | 200.0 | 200.0 | 200.0 | 200.0 |
| $H_2$ flow, ml/min | 64.8 | 64.8 | 64.8 | 64.8 | 64.8 | 129.6 | 97.2 | 64.8 | 64.8 | 64.8 | 64.8 | 64.8 |
| Temp, °C. | 150.0 | 184.0 | 125.0 | 113.0 | 115.0 | 127.0 | 150.0 | 150.0 | 184.0 | 150.0 | 175.0 | 100.0 |
| Reaction time, hr | 4.5 | 5.5 | 5.5 | 5.5 | 2.75 | 6.5 | 5.0 | 5.0 | 5.0 | 3.5 | 5.01 | 5.0 |
| Recovered Products, g | | | | | | | | | | | | |
| Total | 6.5 | 8.14 | 7.83 | 7.41 | 3.92 | 13.62 | 10.5 | 5.01 | — | 4.56 | 5.61 | 2.21 |
| Urea | 2.2 | 2.95 | 2.65 | 2.92 | 2.2 | 2.24 | 3.23 | 2.8 | — | 0.96 | 0.25 | 0.08 |
| $(NH_4)_2CO_3H_2O$ | 4.3 | 4.08 | 4.75 | 4.5 | 1.7 | 8.8 | 5.6 | 2.2 | — | 3.6 | 5.28 | 2.13 |
| Biuret cyanurate | — | — | — | — | — | — | — | — | — | — | — | — |

TABLE 2-continued

| | Examples | | | | | | | | | | | |
|---|---|---|---|---|---|---|---|---|---|---|---|---|
| | 9 | 10 | 11 | 12 | 13 | 14 | 15 | 16 | 17 | 18 | 19 | 20 |
| Triuret[1] | T | T | T | T | T | T | T | T | — | T | T | — |
| % N, recovered | 38.0 | 35.0 | 36.0 | 37.0 | 43.0 | 40.0 | 47.0 | 30.0 | — | 31.0 | 33.0 | 9.0 |

[1]T = Trace

EXAMPLE 17

This experiment was run as in example 9 supra, except that the catalyst consisted of 5% palladium on carbon alone. No solid products were obtained (see Table 2 supra).

EXAMPLES 18-20

These experiments were run as in Example 11 supra, except that 5% palladium on alumina was used as the catalyst. Substantially reduced yields of urea were obtained (see Table 2 supra).

EXAMPLES 21 and 22

These experiments were run as in Example 1 supra, except that the solvent bubblers were filled with water in the place of methanol and in experiment 21, hydrogen was also added as a source of hydrogen. The catalyst, conditions, and results of these experiments are given in Table 3 infra.

TABLE 3

| | Examples | |
|---|---|---|
| | 21 | 22 |
| Experimental Conditions | | |
| Catalyst, 0.5 g | 5% $Rh/Al_2O_3$ | |
| NO flow, ml/min | 32.4 | 32.4 |
| CO flow, ml/min | 200.0 | 200.0 |
| $H_2$ flow, ml/min | 64.8 | — |
| $H_2O$ flow, ml/min | 4.4 | 4.4 |
| Temp, °C. | 217.0 | 202.0 |
| Reaction time, hr | 5.5 | 5.5 |
| Recovered Products, g | | |
| Total | 6.07 | 1.47 |
| Urea | 2.15 | .82 |
| $(NH_4)_2CO_3H_2O$ | 3.92 | .64 |
| Biuret | — | — |
| cyanurate | | |
| Triuret | — | — |
| % N, recovered | 29.0 | 8.0 |

While we have shown and described particular embodiments of our invention, modifications and variations thereof will occur to those skilled in the art. We wish it to be understood, therefore, that the appended claims are intended to cover such modifications and variations which are within the true scope and spirit of our invention.

What we claim as new and desire to secure by Letters Patent of the United States is:

1. A process for the production of urea and its derivatives by reacting CO, NO, and a hydrogen source in the vapor phase, at temperatures of about 75° C. to 225° C. and at pressures of about 1 atmosphere in contact with a catalyst comprising a noble metal selected from the group consisting of palladium, rhodium, and mixtures thereof on an inert support.

2. The process of claim 1 wherein the hydrogen source is hydrogen.

3. The process of claim 1 wherein the hydrogen source is a compound containing hydrogen, and is selected from the group consisting of alkane, alcohol, water, ammonia, and mixtures thereof.

4. The process of claim 3 wherein the hydrogen source is methanol.

5. The process of claim 3 wherein the hydrogen source is water.

6. The process of claim 1 wherein the reaction is initiated at temperatures of 75° C. to 150° C., and allowed to continue with no additional heat supplied.

7. The process of claim 6 wherein said temperature of initiation is about 100° C.

8. The process of claim 1 wherein the catalyst is selected from the group consisting of palladium, rhodium, and mixtures thereof and is supported on alumina.

9. The process of claim 1 wherein the vapor mixture of CO, methanol, and NO are preheated to a temperature in the range from about 0° C. to about 65° C.

* * * * *